United States Patent [19] [11] 4,366,151
Oppenlaender et al. [45] Dec. 28, 1982

[54] OXYALKYLATED FATTY ACIDS AND THEIR USE AS SOLUBILIZERS

[75] Inventors: Knut Oppenlaender, Ludwigshafen; Heinz Krapf, Gruenstadt; Siegfried Lang, Ludwigshafen, all of Fed. Rep. of Germany

[73] Assignee: BASF Aktiengesellschaft, Fed. Rep. of Germany

[21] Appl. No.: 292,166

[22] Filed: Aug. 12, 1981

Related U.S. Application Data

[63] Continuation of Ser. No. 124,989, Feb. 27, 1980, abandoned.

[51] Int. Cl.$^3$ .......................... A61K 31/56; C09F 5/08
[52] U.S. Cl. .................................. 424/238; 260/410.6; 424/244; 424/284; 424/331; 424/344
[58] Field of Search ..................... 260/410.6; 424/238, 424/244, 284, 331, 344

[56] References Cited

PUBLICATIONS

BASF Technical Leaflet, "Cremophor RH Grades" (Apr. 1978).
Lorenz et al., *Agents and Action*, vol. 7/1 (1977), pp. 63–67.

*Primary Examiner*—Thomas A. Waltz
*Attorney, Agent, or Firm*—Keil & Witherspoon

[57] ABSTRACT

Reaction of monohydroxy-fatty acids of the formula $$CH_3-(CH_2)_m-CHOH-(CH_2)_n-COOH$$

where m is an integer from 4 to 9 and n is an integer from 6 to 11, with from 12 to 20 moles of ethylene oxide, the products thus obtained, and their use as solubilizers.

4 Claims, No Drawings

OXYALKYLATED FATTY ACIDS AND THEIR USE AS SOLUBILIZERS

This is a continuation, of application Ser. No. 124,989, filed Feb. 27, 1980, now abandoned.

Solubilizers are required to prepare aqueous injection solutions of water-insoluble active compounds. The substances used for this purpose are reaction products of castor oil, hydrogenated castor oil or sorbitan esters with ethylene oxide, but these exhibit certain disadvantages in use.

For example, a 30% strength aqueous solution of a solubilizer of the above type has a viscosity of from 35 to 40 mPas, and is therefore too viscous for many applications, for example for parenteral administration. A further disadvantage of conventional solubilizers is that after parenteral administration they cause liberation of histamine, entailing a drop in blood pressure.

We have found compounds which do not show these disadvantages.

The invention relates to reaction products of monohydroxy-fatty acids of the formula I

$$CH_3-(CH_2)_m-CHOH-(CH_2)_n-COOH \quad I$$

where m is an integer from 4 to 9 and n is an integer from 6 to 11, with from 12 to 20 moles of ethylene oxide.

The products obtained consist, very predominantly, of substances of the formula II:

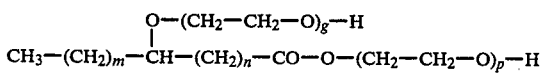

$$CH_3-(CH_2)_m-\underset{\underset{H}{|}}{\overset{O-(CH_2-CH_2-O)_g-H}{C}}H-(CH_2)_n-CO-O-(CH_2-CH_2-O)_p-H \quad II$$

where m and n have the above meanings and the sum of g+p may have any value from 12 to 20.

Preferred reaction products are obtained from monohydroxy-fatty acids of the formula I, where m is an integer from 5 to 8 and n is an integer from 7 to 10, with from 14 to 17 moles of ethylene oxide.

The invention further relates to a process for the preparation of the said oxyalkylated fatty acids, wherein a monohydroxy-fatty acid of the formula II is reacted with from 12 to 20, preferably from 14 to 17, moles of ethylene oxide in the presence of a basic catalyst.

The reaction of the fatty acid with ethylene oxide is carried out by conventional methods in a stirred autoclave under a pressure of from 3 to 9 bar at from 90° to 130° C., preferably from 100° to 120° C. (cf. Schönfeldt: Grenzflächenaktive Äthylenoxid-Addukte, Wissenschaftl. Verlagsgesellschaft Stuttgart, 1976; German Published Application DAS 1,901,535).

Suitable basic catalysts are, in particular, alkali metal hydroxides and alkali metal alcoholates, as well as amines. Amine oxides may also be used. Examples of such catalysts are sodium hydroxide, potassium hydroxide, sodium methylate, potassium methylate, sodium ethylate, potassium ethylate, dimethyldodecylamine and dimethyldodecylamine oxide.

The base which acts as the catalyst during the reaction is neutralized, after completion of the reaction, with a physiologically acceptable acid.

The invention in particular relates to the use of the novel compounds as solubilizers, preferably for pharmaceutical purposes.

The novel compounds are used as solubilizers by conventional methods. For example, the active compound is mixed with the solubilizer and water is added, with or without gentle heating. Examples of suitable active compounds to use in conjunction with the novel compounds are fat-soluble vitamins (vitamins A, E and K), steroids and benzodiazepines.

The viscosity of the 30% strength aqueous solution of the novel compounds is from 3.5 to 15 mPas and is thus substantially lower than that of corresponding solutions of the conventional solubilizers polyoxyethylene(20-)sorbitan monooleate, glycerol polyglycol ricinoleate and glycerol polyglycol hydroxystearate. In addition, the novel substances, in contrast to the conventional solubilizers, do not cause any liberation of histamine after parenteral administration to mammals, and hence also do not cause a drop in blood pressure.

EXAMPLE 1

156 parts by weight (0.52 mole) of a mixture of 9- and 10-hydroxystearic acids are reacted with 343 parts by weight (7.8 moles) of ethylene oxide in the presence of 1.5 parts by weight of KOH powder in a conventional manner in an autoclave at 110°–120 C. A yellowish viscous liquid is obtained. The KOH powder used as the catalyst is neutralized with phosphoric acid. The reaction product has a saponification number of 60, a hydroxyl number of 123 and a viscosity of 8.2 mPas in 30% strength solution in water.

A 1% strength solution of this substance in 5% strength sodium chloride solution has a cloud point of 51°–52° C.

EXAMPLE 2

165 parts by weight (0.55 mole) of 12-hydroxystearic acid are reacted with 339 parts by weight (7.7 moles) of ethylene oxide in the presence of 0.5 part by weight of a 50% strength KOH solution in an autoclave at 100°–110° C. An almost colorless soft paste is obtained. The potassium hydroxide is neutralized with acetic acid. The reaction product has a melting point of 25°–26° C., a saponification number of 61, a hydroxyl number of 125 and a viscosity of 11.5 mPas in 30% strength solution in water. The cloud point of a 1% strength solution of the product in 5% strength sodium chloride solution is 54°–55° C.

EXAMPLE 3

1,050 parts by weight (3.5 moles) of 12-hydroxystearic acid are reacted with 154 parts by weight (3.5 moles) of ethylene oxide in the presence of 31.5 parts by weight of N,N-dimethyldodecylamine as the catalyst, in an autoclave at 100°–110° C. 176.5 parts by weight of the resulting yellowish solid substance, which contains 1 mole of ethylene oxide per mole of 12-hydroxystearic acid, are reacted with 330 parts by weight (7.5 moles) of ethylene oxide in the presence of 1.8 parts by weight of KOH powder in an autoclave at 100°–110° C. A pale yellowish soft paste is obtained, which is brought to pH 7 with acetic acid. The reaction product has a saponification number of 54, a hydroxyl number of 123 and a viscosity of 6.5 mPas in 30% strength solution in water.

The cloud point of a 1% strength solution of the product in 5% strength sodium chloride solution is 57°–58° C.

USE EXAMPLES (a) 500 mg of propanidide are mixed, at 50°–60° C., with 2 g of the oxyethylation product obtained as described in Example 1. 7.5 ml of water are added at the same temperature, whilst stirring. A clear aqueous solution having a viscosity of 9 mPas (Pas=Pascal seconds) is obtained.

(b) 1 g of vitamin E acetate is mixed with 2 g of the solubilizer obtained according to Example 2 and the mixture is heated to 50°–60° C. and slowly mixed with 7 ml of water at this temperature. The resulting clear solution has a viscosity of 4.5 mPas.

(c) 1.5 g of azulene are mixed with 2.0 g of a solubilizer according to Example 3 and then with 6.5 ml of water, whilst heating gently. A clear, deep blue aqueous solution of viscosity of 4.8 mPas is obtained.

(d) 800 mg of vitamin $K_1$ are mixed with 2 g of solubilizer according to Example 3. The mixture is heated to 60° C. and 7.5 ml of water at the same temperature are slowly added. The clear vitamin $K_1$ solution has a viscosity of 4 mPas.

We claim:

1. The product of the reaction of a monohydroxy-fatty acid of the formula I

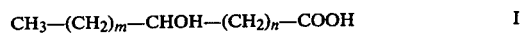

$$CH_3-(CH_2)_m-CHOH-(CH_2)_n-COOH \qquad I$$

where m is an integer from 4 to 9 and n is an integer from 6 to 11, with from 12 to 20 moles of ethylene oxide.

2. A product as claimed in claim 1, which has the formula II

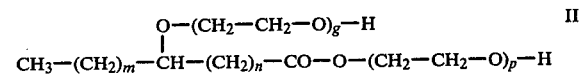

$$CH_3-(CH_2)_m-\underset{\underset{\displaystyle O-(CH_2-CH_2-O)_g-H}{|}}{CH}-(CH_2)_n-CO-O-(CH_2-CH_2-O)_p-H \qquad II$$

where m and n have the meanings given in claim 1 and the sum of g′p is any number from 12 to 20.

3. A pharmaceutical product comprising a water-insoluble active component, water and as a solubilizer for said active component, an effective amount of a compound of formula I of claim 1.

4. The product of claim 1 wherein the compound of formula I is reacted with from 14 to 17 moles of ethylene oxide.

* * * * *

UNITED STATES PATENT AND TRADEMARK OFFICE
CERTIFICATE OF CORRECTION

PATENT NO. : 4,366,151
DATED : December 28, 1982
INVENTOR(S) : Knut Oppenlaender et al.

It is certified that error appears in the above-identified patent and that said Letters Patent is hereby corrected as shown below:

On the title page, insert:

--- /30/ Foreign Application Priority Data

March 22, 1979    Germany.......2911241  ---.

Signed and Sealed this

Twenty-sixth Day of February 1985

[SEAL]

*Attest:*

DONALD J. QUIGG

*Attesting Officer*    *Acting Commissioner of Patents and Trademarks*